(12) United States Patent  
Wang et al.

(10) Patent No.: US 9,400,286 B2  
(45) Date of Patent: Jul. 26, 2016

(54) APPARATUS AND METHOD FOR ANALYZING SAMPLES

(71) Applicant: SHENZHEN MINDRAY BIO-MEDICAL ELECTRONICS CO., LTD., Shenzhen (CN)

(72) Inventors: Zhihong Wang, Shenzhen (CN); Zhi Xu, Shenzhen (CN); Chuanfen Xie, Shenzhen (CN); Feng Li, Shenzhen (CN)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 0 days.

(21) Appl. No.: 14/625,483

(22) Filed: Feb. 18, 2015

(65) Prior Publication Data

US 2015/0247875 A1  Sep. 3, 2015

Related U.S. Application Data

(62) Division of application No. 12/257,323, filed on Oct. 23, 2008, now abandoned.

(30) Foreign Application Priority Data

Oct. 23, 2007  (CN) .......................... 2007 1 0166628

(51) Int. Cl.
  *G01N 35/02*  (2006.01)
  *G01N 35/00*  (2006.01)
  *G01N 35/10*  (2006.01)

(52) U.S. Cl.
  CPC .......... *G01N 35/025* (2013.01); *G01N 35/0092* (2013.01); *G01N 35/1002* (2013.01);

(Continued)

(58) Field of Classification Search
  CPC .................... G01N 35/0092; G01N 35/00584; G01N 35/025; G01N 35/02; G01N 35/1002; G01N 35/1004; G01N 35/10; G01N 2035/1032; G01N 2035/1027; Y10T 436/11; Y10T 436/111666; Y10T 436/13
  USPC ................................................ 436/27, 45, 43
  See application file for complete search history.

(56) References Cited

U.S. PATENT DOCUMENTS

| 3,819,271 A | 6/1974 | Beug et al. |
| 4,285,594 A | 8/1981 | Butts et al. |

(Continued)

FOREIGN PATENT DOCUMENTS

| CN | 1409102 A | 4/2003 |
| CN | 2651746 | 10/2004 |

(Continued)

OTHER PUBLICATIONS

Non-final Office Action dated Jun. 21, 2013 for U.S. Appl. No. 12/257,301.

(Continued)

*Primary Examiner* — Christine T Mui  
(74) *Attorney, Agent, or Firm* — Kory D. Christensen; Stoel Rives LLP (57) ABSTRACT

A sample analyzer comprises a reaction tray, a sample/reagent tray, and a probe. The reaction tray performs a first number of stops and rotations during an operating cycle, wherein the first number is configured to cause each of the reaction vessels to stop once at a position for the test before any of the number of the reaction vessels stops at the position for a second time. The sample/reagent tray rotates one of a sample container and reagent containers to a sample/reagent retrieving position during an operating cycle. The probe dispenses test sample(s), first reagent, and second reagent during different periods in different stop periods during an operating cycle. A method for analyzing samples is also disclosed.

11 Claims, 5 Drawing Sheets

(52) U.S. Cl.
    CPC .... *G01N35/1004* (2013.01); *G01N 2035/1032* (2013.01); *Y10T 436/111666* (2015.01); *Y10T 436/113332* (2015.01); *Y10T 436/114998* (2015.01)

(56) References Cited

U.S. PATENT DOCUMENTS

| | | | |
|---|---|---|---|
| 4,477,190 | A | 10/1984 | Liston et al. |
| 4,908,320 | A | 3/1990 | Zakowski et al. |
| 7,113,282 | B2 | 9/2006 | Aguirre et al. |
| 2003/0044990 | A1 | 3/2003 | Seto |
| 2003/0072680 | A1 | 4/2003 | Higuchi et al. |

FOREIGN PATENT DOCUMENTS

| | | |
|---|---|---|
| CN | 1624484 A | 6/2005 |
| CN | 2807259 | 8/2006 |
| CN | 1963527 A | 5/2007 |
| CN | 101059506 A | 10/2007 |
| CN | 101140224 A | 3/2008 |
| EP | 289789 | 11/1988 |
| EP | 0316766 A2 | 5/1989 |
| JP | 55-114955 | 9/1980 |
| JP | 9-297144 A | 11/1997 |
| JP | 11-2566 A | 1/1999 |
| JP | 2007024911 A | 2/2007 |

OTHER PUBLICATIONS

Office Action dated Apr. 4, 2011 for U.S. Appl. No. 12/257,301.
Final Office Action dated Aug. 31, 2011 for U.S. Appl. No. 12/257,301.
English Abstract of CN 101140224, Mar. 2008 (publication of CN document).
International Search Report for Chinese Patent Application No. 200710166617.0, 2008.
English abstract for JP55-114955, 1980.
English abstract for JP11-2566, 1999.
Chinese Search Report for Chinese Patent Application No. 200710166628.9, 2008.
English Abstract for Application No. JP2007024911, 2007.
English Abstract for Application No. JP9297144, 1997.
English Abstract for Application No. 1963527, CN 1963527. 2007.
English Abstract for Application No. CN1624484, 2005.
English Abstract for Application No. CN101059506, 2007.
Xu "Color technical principle and its application to dyeing and finishing (XIV)" State Key Lab of Modem Optical Instrumentation, Zhejiang University, 2006; No. 7, pp. 40-43.
Wang "Technical Issues of the Operation of the Hitachi 260-50 IR Spectrophotometer" 1986, vol. 3, No. 1; 4 pages.
Modern Preventive Medicine, 2006, vol. 33, No. 4, pp. 577-578.
Journal of Natural Science of HeLong Gjiang Unviversity, Apr. 2006, vol. 23, No. 2, pp. 202-205.
Development Progress of Clinical Analytical and Diagnostic Bio-Medical Equipment, Medical Devices and Health Care, Jun. 15, 1998, pp. 39-47.

APPARATUS AND METHOD FOR ANALYZING SAMPLES

CROSS-REFERENCE TO RELATED APPLICATIONS

This application is a division of U.S. patent application Ser. No. 12/257,323, filed Oct. 23, 2008, which claims the benefit of Chinese Patent Application No. 200710166628.9, filed Oct. 23, 2007. The content of each of these applications is incorporated herein by reference.

TECHNICAL FILED

This disclosure relates generally to a field of sample testing and analyzing and to methods and apparatus for analyzing samples.

BRIEF SUMMARY

Various embodiments relate to a sample analyzer that may achieve a constant speed for testing both the single and the double-reagent items by using a simple structural configuration.

Some embodiments are directed at to a method for analyzing samples.

A sample analyzer in some embodiments comprises a reaction tray, a sample/reagent tray, and a probe. The reaction tray is for placing a loop of reaction vessels in some embodiments. In some embodiments, a plurality of reaction vessels may be arranged in the form of a loop. In these embodiments where the sample analyzer comprises a plurality of reaction vessels arranged in a loop, during at least one operating cycle which starts from the time for performing a previous sample dispensing till the time for performing the next sample dispensing on the loop of the reaction vessels, the reaction tray stops at least three times and rotates or spins at least three times, wherein the number of rotated vessel positions minus the number of rotated integral loop(s) of vessel positions during each of the three times of rotation is of a fixed value, and the number of rotated vessel positions during all the three times of rotation is equal to the number ofRloop(s) of vessel positions plus or minus one.

In some embodiments, R constitutes an integer. In some embodiments, R is greater than or equal to one. In some embodiments, the sample/reagent tray is configured for accommodating a sample container and reagent containers and for rotating one of the sample container and reagent containers to the sample/reagent pipet position as needed in each operating cycle. In some embodiments, the probe performs the sample dispensing operation sequence, the first reagent dispensing operation sequence, and the second reagent dispensing operation sequence during different periods of time within an operating cycle as needed. In some embodiments, the sample dispensing of the sample dispensing operation sequence, the first reagent dispensing of the first reagent dispensing operation sequence, and the second reagent dispensing of the second reagent dispensing operation sequence may be accomplished in their respective different stop periods of the reaction tray. In some embodiments, the automatic sample analyzer may dispense a sample, a first reagent, and a second reagent into one or more reaction vessels while the one or more reaction vessels are disposed in the sample/reagent dispensing position of the reaction tray during their respective stop periods.

A sample analyzing method is also disclosed in accordance with some embodiments. In some embodiments, during an operating cycle starting from the time of performing a previous sample dispensing till the time of performing the next sample dispensing on the reaction vessel loop which comprises one or more reaction vessels and forms an open, closed, or semi-open loop, the method comprises the following actions: (1) enabling the loop of reaction vessels to at least stop three times and to rotate three times, wherein the number of vessel positions in the loop passed during rotation of the loop minus the number of full rotations of the reaction vessels during each of the three times of rotation is of a fixed number and the cumulative total number of vessel positions passed during the three rotations is equal to a number R, where R represents the number of loop(s) of vessel positions plus or minus one; (2) enabling one of a sample container and reagent containers to rotate to the sample/reagent pipet position as needed or required; and (3) performing, at different stages of the analysis, a sample dispensing operation sequence, a first reagent dispensing operation sequence, and a second reagent dispensing operation sequence in some embodiments.

In some embodiments, a sample dispensing operation of the sample dispensing operation sequence, a first reagent dispensing operation of the first reagent dispensing operation sequence, and a second reagent dispensing operation of the second reagent dispensing operation sequence are accomplished in the respective different stop periods of the reaction vessel loop. In some embodiments, a sample, a first reagent, and a second reagent may be dispensed into the reaction vessel(s) which stop at the sample/reagent dispensing position(s) during the respective stop period(s).

The sample analyzer and the method for analyzing samples in accordance with various embodiments may be achieved by using a simple structure without affecting the test performance. Moreover, since the first reagent and the second reagent may be dispensed during a same operating cycle, and thus a particular operating cycle for the dispensing of second reagent may not be needed in some embodiments. Therefore, the sample analyzer or the method for analyzing samples may exhibit identical, substantial identical test speeds or consistent test speeds for testing both single and double-reagent items and a relatively higher test efficiency in various embodiments.

BRIEF DESCRIPTION OF THE DRAWINGS

Various aspects of the sample analyzer and method for analyzing samples may be better understood with reference to the following drawings. The components in the drawings are not necessarily drawn to scale, and the emphasis is placed upon clearly illustrating the principles of the present sample analyzing apparatus and sample analyzing method. The drawings illustrate the design and utility of various embodiments of the invention, in which similar elements are referred to by common reference numerals. In order to better appreciate how advantages and objects of various embodiments of the inventions may be obtained, a more particular description of various embodiments of the inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION

Nowadays, an apparatus or a mechanism for automatic analysis of biochemical analyses (the automatic biochemical analyzer, collectively) is widely used during clinical examination to analyze the clinical chemical constituents of samples which comprises blood serum, blood plasma, urine, cerebrospinal fluid, and so on. The automatic biochemical analyzer may automatically accomplish a series of one or more processes during a biochemical analysis. The series of one or more processes comprise reagent dispensing, sample dispensing, the reagent and sample mixing, incubation of the mixed solution, absorbance measurement, and result calculation, etc. The biochemical analyzer comprises may comprise a reaction tray assembly, an optical measurement system, a sample/reagent tray assembly, a sample/reagent probe assembly, a mixing mechanism, a cleaning assembly, and a user operating system.

The optical measurement system used in the automatic biochemical analyzer may generally be a grating-photometer, a multi-channel static filter photometer, a filter-wheeled photometer, or other devices or mechanisms to achieve similar purposes. Different optical measurement systems may be suitable for biochemical analyzing apparatuses with different test speeds. The filter-wheeled photometer that is often used in the automatic biochemical analyzer has a relatively low cost of ownership, but its test speed is mostly limited due to, for example, its serial data collection for different wavelengths. Therefore, the filter-wheeled photometer is usually used on small automatic biochemical analyzers which are often used in facilities that usually do not demand or require high speed testing devices.

In a conventional automatic biochemical analyzer that is equipped with a filter-wheeled photometer, in order to simplify the structural configuration of the automatic biochemical analyzer so as to reduce the cost thereof, such conventional automatic biochemical analyzer often employs one probe to accomplish all the operations of sample dispensing, first reagent dispensing, and second reagent dispensing. Such conventional automatic biochemical analyzer may also employ one sample/reagent tray is used as a receptacle for sample vessels and reagent bottles.

Such conventional automatic biochemical analyzer may also employ one reaction tray for placing reaction vessels. The probe sequentially pipets a first reagent, a sample, and a second reagent, and then dispenses the sample, the first reagents, and the second reagents together into a reaction vessel so as to allow the sample and the reagents to be mixed by injection mixing. Although the structural configuration of the automatic biochemical analyzer may be greatly simplified and the cost may thus be reduced as a result, the uniformity of the mixture due to injection mixing may not be sufficiently good and may more likely negatively affects the test performance of the automatic biochemical analyzer.

In some other prior art approaches, the automatic biochemical analyzer often employs an independent stirring rod for stirring and mixing operations so that the test performance may be more predictable or consistent. However, such schemes of using a single probe generally may not exhibit a substantially constant test speed for testing both single and double-reagent items, i.e., a particular cycle is needed to dispense the second reagent. One of ordinary skills in the art will clearly understand that the test speed for single-reagent items and that for double-reagent items may deviate from each other from the same analyzer or from different analyzers due to manufacturing or operational allowances or tolerances or car and tear of the analyzer even though both test speeds are intended or designed to be the same.

Furthermore, for such a biochemical analyzer, during the operating cycle for dispensing the second reagent, not only the operation of first reagent dispensing but also the sample dispensing operation often may not be accomplished. As a result, a time conflict exists in dispensing the sample and dispensing the second reagent, and it is thus necessary to prioritize the sample dispensing for a certain item or the second reagent dispensing for a certain item according to priorities established in the biochemical analyzer. Therefore, the second reagent dispensing or the sample dispensing for another item may have to be delayed. As a result, there may exhibit no consistency or repeatability in the processes or results of the same test item with different combinations of test items. Accordingly, such an operating method of non-constant speed for testing both single and double-reagent items may adversely affect the repeatability of clinical test results.

As disclosed in U.S. Pat. No. 4,908,320, an operating method of an automatic biochemical analyzer is disclosed. The automatic biochemical analyzer comprises an independent sample dispensing mechanism and a reagent dispensing mechanism (i.e., two probes) for accomplishing the tasks of sample dispensing and reagent dispensing respectively. Nonetheless, it still does not achieve a constant speed for testing both the single and the double-reagent items and therefore needs a particular operating cycle to perform the operation of dispensing the second reagent. With this type of automatic biochemical analyzers, although the dispensing of the samples and second reagent dispensing for all test items is not delayed, and the repeatability of test process may be ensured, these automatic biochemical analyzers may cause the issues where not only the dispensing of the first reagent may be delayed, but also a reaction vessel which needs to be manipulated to a reagent dispensing position to allow a first reagent to be dispensed thereinto may be unused during the dispensing of the second reagent. Therefore, if there is a double-reagent item under test, the reaction vessels loaded on the reaction tray may not be continuously in use. Furthermore, if there exist many double-reagent items under test, the test efficiency may be significantly lowered.

With regard to the requirement for a particular operating cycle for dispensing the second reagent, in addition to the aforementioned drawbacks, the complexity of such an automatic biochemical analyzer is also increased because the operating cycle for dispensing the second reagent is different from that for dispensing the first reagent.

In addition, another type of such conventional automatic biochemical analyzer uses at least two probes to respectively accomplish the operation of sample dispensing and the operation of first reagent and second reagent dispensing during one operating cycle. Some of such conventional automatic biochemical analyzer even employs two stirring rods which are configured to respectively accomplish the operations of sample stirring and second reagent stirring. Nonetheless, for those biochemical analyzers that are equipped with a filter-wheeled photometer, the test speed thereof is relatively low due to the limit on the manner of which the photoelectric data are collected. With regard to such a biochemical analyzer which exhibits different test speeds, although the configuration of two probes and even two stirring rods may achieve a constant speed for testing both the single and the double-reagent items, the cost of such a biochemical analyzer is nonetheless higher.

In addition, Chinese Patent No. 96112818.6 has disclosed another automatic biochemical analyzer. In this Chinese patent, the automatic biochemical analyzer employs two probes and one stirring rod so as to achieve constant speed for testing both the single and the double-reagent items. Nonetheless, because the automatic biochemical analyzer employs two probes, the cost is still high.

Therefore, there exist a need for an automatic sample analyzer and a method for analyzing samples that overcome the aforementioned drawbacks.

Reference will now be made to the figures to describe various embodiments of the apparatus and the method for analyzing samples.

Figure 1:
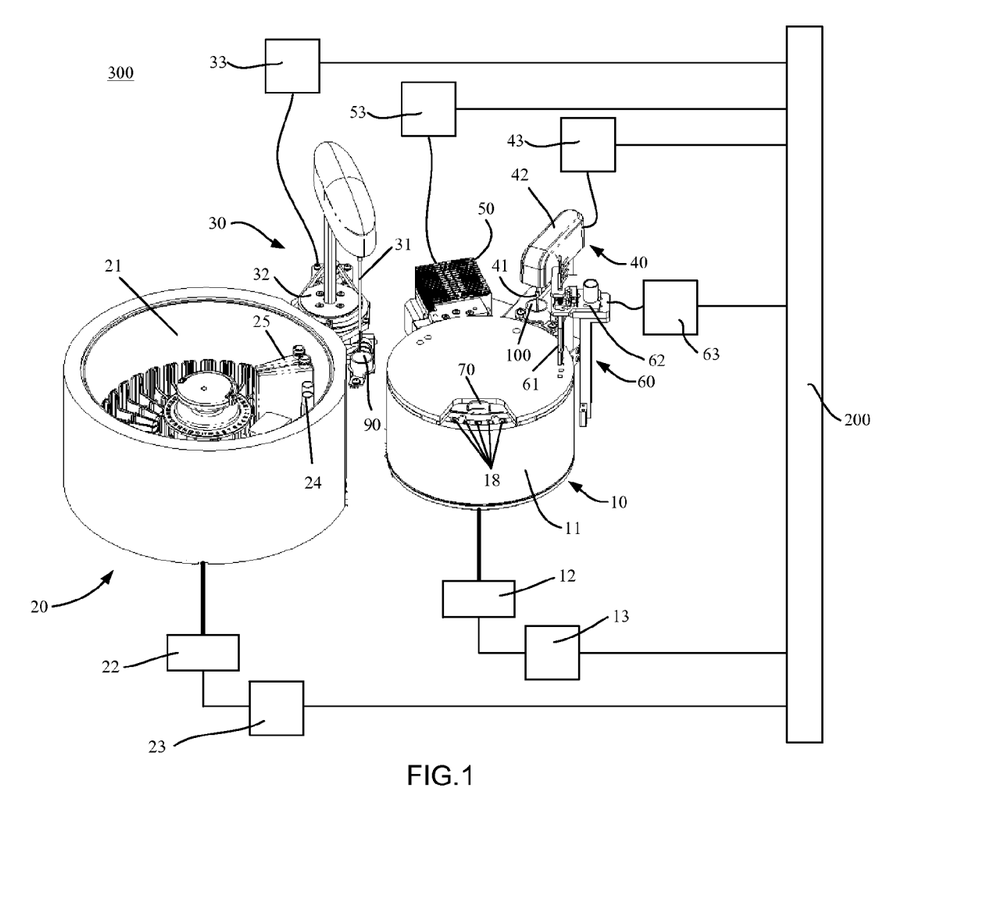
FIG. 1 illustrates a schematic diagram showing the basic structure of a sample analyzing apparatus in accordance with some embodiments.

Referring to FIG. 1, a sample analyzing apparatus 300 in accordance with an embodiment of the present invention comprises a reaction tray assembly 10, a sample/reagent tray assembly 20, a probe assembly 30, a stirring assembly 40, an optical detector 50, a data collection and processing device 53, and a user operating system 200 in some embodiments. The reaction tray assembly 10 comprises a reaction tray 11, a drive mechanism 12, and a controller 13 in some embodiments.

The sample/reagent tray assembly 20 comprises a sample/reagent tray 21, a drive mechanism 22, and a controller 23 in some embodiments. The probe assembly 30 comprises a probe 31, a drive mechanism 32, and a controller 33 in some embodiments. The stirring assembly 40 comprises a stirring rod 41, a drive mechanism 42, and a controller 43 in some embodiments. The optical detector 50 may be electrically coupled to the data collection and processing device 53 in some embodiments. The user operating system 200 may act as a human-machine interaction interface and may communicate with the controllers, 13, 23, 33, 43, and the data collection and processing device 53 in some embodiments.

In addition or in the alternative, according to different designs, the sample analyzer 300 may be configured to operate automatically for cleaning the reaction vessels in some embodiments. In these embodiments, the sample analyzer 300 further comprises an automatic reaction vessel cleaning assembly 60. The automatic reaction vessel cleaning assembly 60 comprises the automatic cleaning head 61, a drive mechanism 62, and a controller 63 in some embodiments.

The controller 63 may communicate with the user operating system 200 in some embodiments. The sample analyzing apparatus 300 may also be configured for manual reaction vessel replacement, wherein the aforementioned automatic reaction vessel cleaning assembly 60 may be omitted, and a manual reaction vessel replacement mechanism 70 may be employed to make the operation of manual reaction vessel replacement more convenient in some embodiments. For the ease of illustration and/or explanation, both the automatic reaction vessel cleaning assembly 60 and the manual reaction vessel replacement mechanism 70 are shown in FIG. 1. Nonetheless, one or ordinary skills in the art would clearly understand that the sample analyzer 300 may comprise either the automatic reaction vessel cleaning assembly 60 or the manual reaction vessel replacement mechanism 70 in some embodiments.

In the illustrated embodiments as shown in FIG. 1, the reaction tray 11 may be disposed on the right side on a working platform of the sample analyzer 300 in some embodiments.

Figure 2:
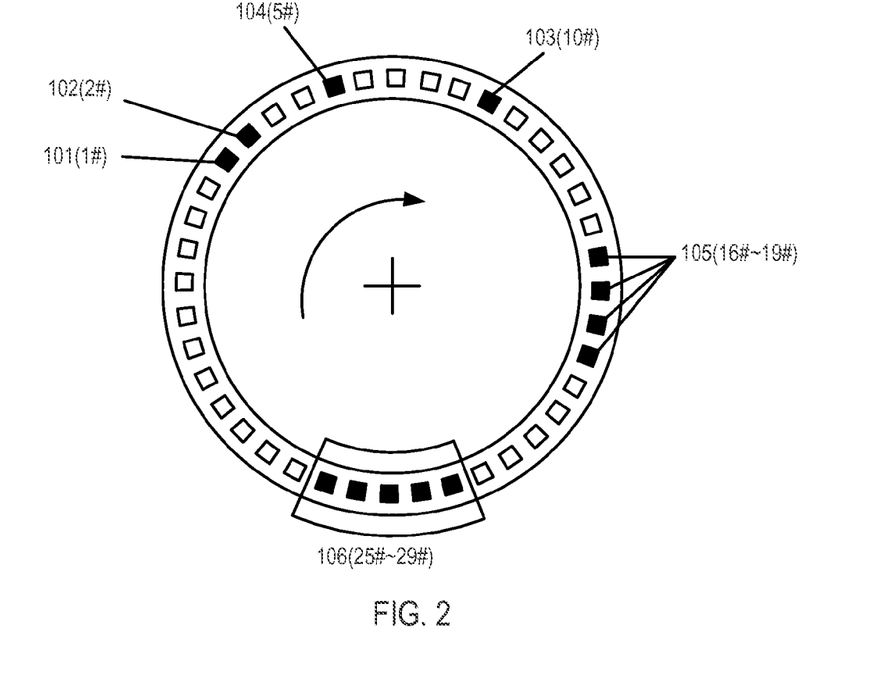
FIG. 2 illustrates operating positions of the reaction tray of the sample analyzer of FIG. 1 in some embodiments.

Referring to FIG. 2 where forty reaction vessels 18 are equidistantly arranged along a circumference of the reaction tray 11 in some embodiments. At least some of the reaction vessels 18 act as both a container and a colorimetric vessel for the reaction solution in some embodiments. At least some of the reaction vessels 18 may be disposable in embodiments with manual reaction vessel replacement or may be semi-permanent in embodiments with automatic reaction vessel cleaning. The reaction tray 11 may be configured to be driven by the drive mechanism 12 and the controller 13 to rotate and/or stop in some embodiments. In some embodiments, the drive mechanism 12 comprises a stepped motor. The reaction tray 11 comprises a temperature control system for maintaining the reaction solution in at least some of the reaction vessels 18 at a certain temperature in some embodiments. In some embodiments, the temperature control system maintains at least some of the reaction vessels 18 at about 37 degrees Celsius.

The sample/reagent tray 21 may be disposed on the left side on the working platform of the sample analyzer 300 in some embodiments.

Figure 3:
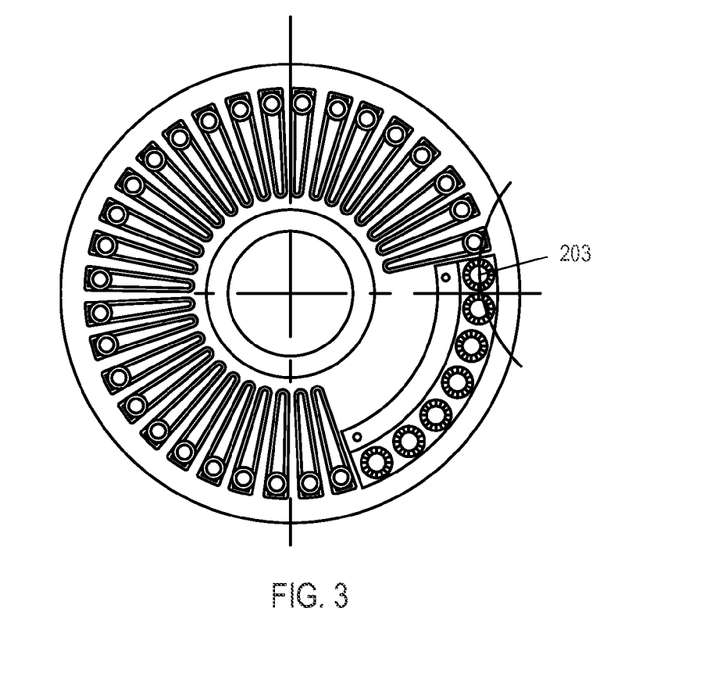
FIG. 3 illustrates operating positions of the sample/reagent tray of the sample analyzer of FIG. 1 in some embodiments.

Referring to FIG. 3, thirty six operating positions may be equidistantly arranged along a circumference of the sample/reagent tray 21 in some embodiments. Each of the thirty six operating positions may act as a sample position or a reagent position in some embodiments. The sample positions and the reagent positions may be respectively used to place or accommodate sample containers 24 and reagent containers 25 in some embodiments. The sample containers 24 and the reagent containers 25 may be respectively configured for containing or accommodating one or more samples and/or one or more reagents used in various biochemical tests in some embodiments. The sample/reagent tray 21 may be configured to be driven by the drive mechanism 22 and the controller 23 to rotate and/or stop in some embodiments.

The probe 31 may be disposed at a certain position between the sample/reagent tray 21 and the reaction tray 11 so that the trace of the tip of the probe 31 during rotation may pass through the sample/reagent suction position 203 of the sample/reagent tray, the sample dispensing position 101 of the reaction tray, the diluted sample suction position 102 of the reaction tray, and the position of probe cleaning cell 90 in some embodiments. The probe 31 may perform the actions of sucking and dispensing of sample(s) and reagent(s) as required in a biochemical test in some embodiments. After each time of sucking and dispensing of sample or reagent, one or more actions for cleaning the inner and outer walls of the probe are performed in the probe cleaning cell 90 in some embodiments.

Referring back to FIG. 2. The operating position diagram of the reaction tray further illustrates the operating positions of respective parts in some embodiments. The sample dispensing position 101 of the reaction tray 11 may be defined as 1# position. The serial number of positions of the reaction tray sequentially increases in the clockwise direction in some embodiments or in the counterclockwise direction in some other embodiments. The diluted sample suction position 102 may be defined as the 2# position or counterclockwise. The photoelectric measurement position 104 may be defined as the 5# position or counterclockwise. The stirring position 103 may be defined as the 10# position or counterclockwise. The reaction vessel cleaning positions 105 may be defined as the 16# to 19# positions or counterclockwise. The manual reaction vessel-replacing positions may be defined the 25# to 29# positions or counterclockwise.

The stirring rod 41 may be disposed at the outside of the reaction tray 11 or counterclockwise. A trace of the stirring rod 41 during motion may reach the position of the stirring rod cleaning cell 100 and the stirring position 103 of the reaction tray or counterclockwise. The stirring rod 41 may perform the actions of stirring and mixing after the operations of sample dispensing and second reagent dispensing in some embodiments. After each time the stirring action is performed, the stirring rod moves to the stirring rod cleaning cell 100 for cleaning in some embodiments.

The optical detector 50 may be disposed at the outside of the reaction tray 11 and between the probe 31 and the stirring rod 41 in some embodiments. The optical detector 50 performs a photoelectric data measurement for reaction vessels in some embodiments. The optical detector 50 may comprise a light source, a filter-wheeled photometer, and a photoelectric measurement component in some embodiments. During the operation of the sample analyzer when the reaction vessels sequentially pass through the photoelectric measurement position 104, the optical detector 50 may perform the photoelectric measurement for a particular wavelength with respect to each of the reaction vessels in some embodiments.

With regard to the automatic reaction vessel cleaning action, the automatic cleaning head 61 may be located on the right side of the reaction tray 11 and comprises four stage cleaning heads in some embodiments. The first to the fourth stage cleaning heads may be disposed above the cleaning position 105 of the reaction tray 11 in series in a clockwise direction in some embodiments. The reaction vessel automatic cleaning head 61 may be configured for sequentially performing the cleaning actions of the reaction vessels that have completed the designated test so as to keep the test process continuously running in some embodiments.

With regard to the manual reaction vessel replacement, the automatic reaction vessel cleaning assembly 60 may be omitted in some embodiments. The manual reaction vessel replacement mechanism 70 on the reaction tray 11 may be configured to make it convenient for replacing the used reaction vessels as needed in some embodiments. The manual reaction vessel replacement mechanism 70 may be disposed at the front of the reaction tray 11 in some embodiments. The manual reaction vessel replacement mechanism 70 may comprise a sliding-type light-shielding plate in some embodiments. The light-shielding plate may be opened when the reaction vessels are being replaced, and may be closed after the reaction vessels has been replaced in some embodiments. In some embodiments, the light-shielding plate may be opened by gradually pushing it away.

Based upon the structural configuration of the aforementioned sample analyzer 300, a sample analyzing method in accordance with the present invention is described below in greater details.

A method for analyzing samples may be summarized as a series of operating cycles in some embodiments. In some embodiments, an operating cycle may be defined as the time interval from the beginning of a previous sample dispensing action to the beginning of the next sample dispensing action. The respective parts take actions in each operating cycle according to one or more predetermined operation sequences to accomplish the operations comprising at least one of sample dispensing, first reagent dispensing, second reagent dispensing, stirring, photoelectric data collection, and automatic reaction vessel cleaning in embodiments with the automatic reaction vessel cleaning assembly. In some embodiments, the operating cycle is performed repeatedly, and tests for multiple sample items may be efficiently accomplished.

The respective parts of the sample analyzer 300 repeatedly operate according to the operating cycle(s). During each operating cycle, the respective parts perform the same operation sequence or remain still depending upon the need of the entire test process in some embodiments. In some embodiments where a part may not be needed to perform an operation sequence during a certain operating cycle the operation part remains still during the period during which the operation part usually needs to perform the operation sequence during that operating cycle in some embodiments. The temporal duration for each operating cycle may be identical or substantially identical in some embodiments. One of ordinary skills in the art would clearly understand that two temporal periods may be substantially identical even though they are intended or designed to be exactly identical due to tolerances and allowances in the measurement or during the testing process.

Figure 4:
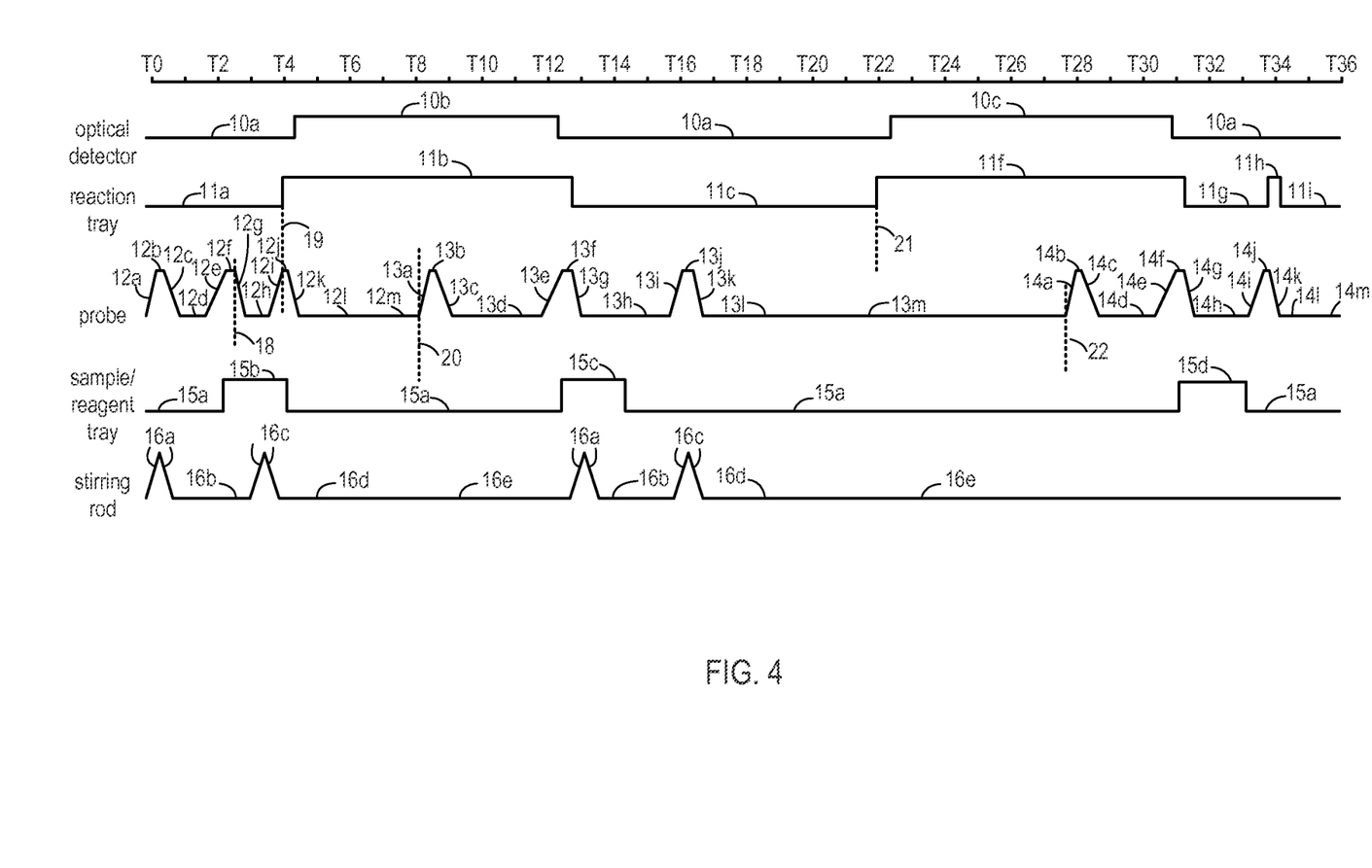
FIG. 4 illustrates a time sequence of some components of the sample analyzer of FIG. 1 when during the operation of a manual reaction vessel-replacement in some embodiments.
Figure 5:
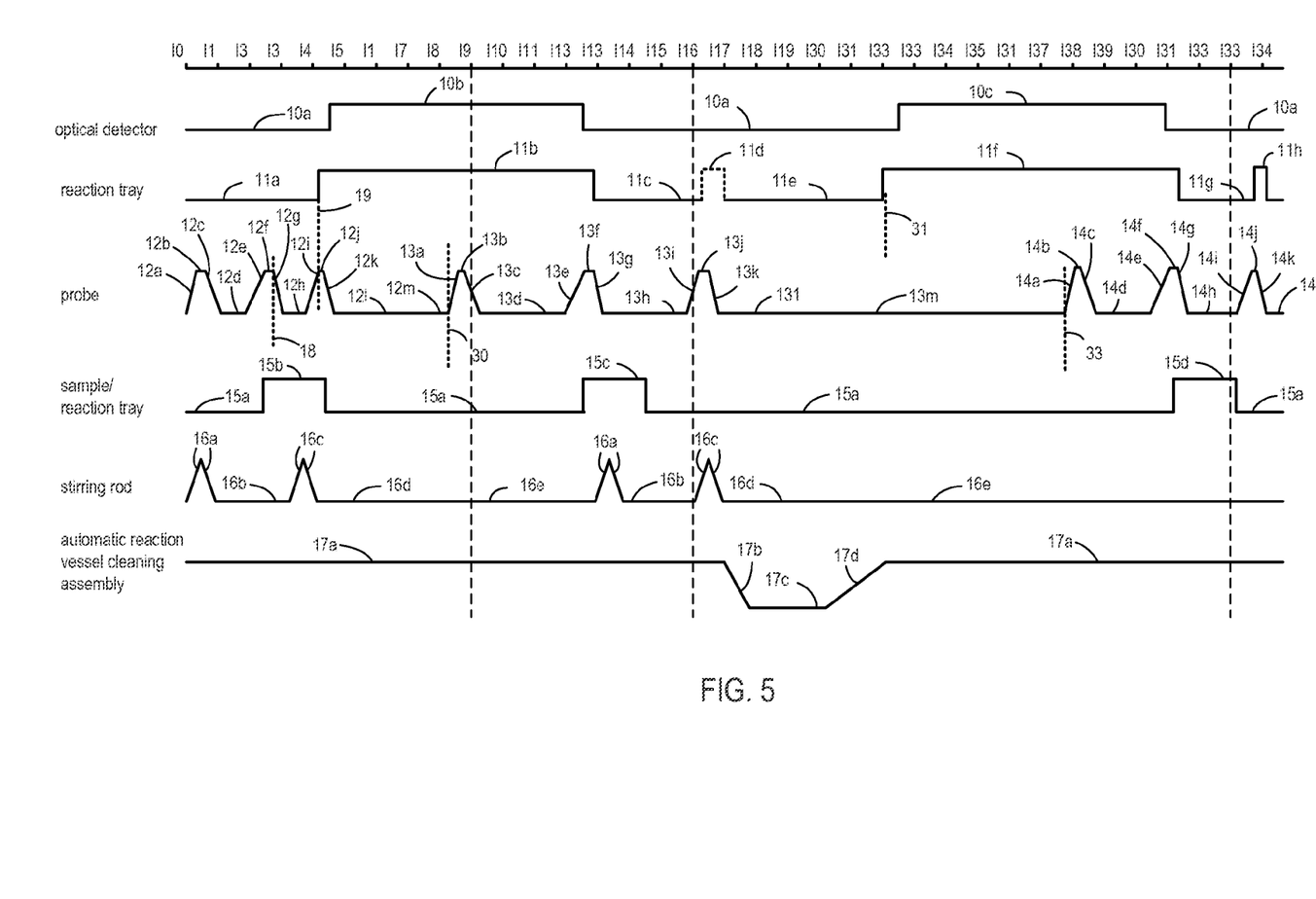
FIG. 5 shows a time sequence of some components of the sample analyzer of FIG. 1 during the operation of an automatic reaction vessel cleaning in some embodiments.

FIGS. 4 and 5 illustrate some operation sequences of certain parts of the sample analyzer during the operating cycle as well as the relationship (also known as time sequence diagram in some embodiments) among these parts of the sample analyzer. Moreover, FIG. 4 illustrates the time sequence diagram in some embodiments where no automatic reaction vessel cleaning assembly 60 is configured. FIG. 5 illustrates the time sequence diagram in some embodiments where the automatic reaction vessel cleaning assembly 60 is configured. The horizontal axis in FIG. 4 and FIG. 5 represents time or the temporal dimension and is labeled to respectively denote different operations.

Firstly, the time sequence of the respective parts in the operating cycle in some embodiments where no automatic reaction vessel cleaning assembly 60 is configured will be described below in details.

During each operating cycle, the reaction tray 11 sequentially performs four times of stop, 11*a*, 11*c*, 11*g*, and 11*i*, and three times of clockwise rotation, 11*b*, 11*f*, and 11*h* in some embodiments. The reaction tray 11 rotates a total of R loop(s), where R is an integer and is greater or equal to one, plus one vessel position in some embodiments. In some embodiments, rotating one vessel position means that the vessel rotates from a position to a next position, e.g., from 1# position to 2# position. In some embodiments, the four times of stop actually constitute three times of stop because the operation sequences in the operating cycle are repeatedly performed such that the stop that occurs at the end of one operating cycle and the stop that occurs at the beginning of the next operating cycle constitute the same stop. That is, in these embodiments, the stop that occurs at the end of one operating cycle may serve as the stop that is needed at the beginning of the next operating cycle. In this figure, such a stop is divided into two times of stop 11*a* and 11*i* for the sole purpose of convenience of illustration and ease of explanation.

A start point of an operating cycle may be any time point. In the illustrated embodiments, the start point is defined as the beginning of the operation sequence of sample dispensing. In those embodiments where the reaction tray rotates three times and makes three stops during each operating cycle, the reaction tray rotates three times and makes three stops during each operating cycle where the reaction tray rotates and passes a first number of positions for the first rotation, and a second number of positions for the second rotation, and a third number of positions for the third rotation such that the total number of positions passed during an operating cycle ensures that each position in the reaction tray will stop at the appropriate position(s) for dispensing of the samples and/or reagents or for stirring or for other purposes of the tests exactly once before any of the vessel or sample/reagent holder stops at the same position(s) for the second time.

In some embodiment where the reaction tray comprises 40 vessels, the reaction tray may rotate and pass nine vessel positions during the first rotation of an operating cycle, 23 vessel positions during the second rotation of an operating cycle, and nine vessel positions during the third rotation of an operating cycle such that the total number of vessel positions passed for one operating cycle is 41 which is one more than the total number of vessel positions. In these embodiments, if the reaction vessel stops at the first vessel position after the first rotation of a first operating cycle the vessel will stop at the second vessel position after the first rotation of the second operating cycle, and so forth. In these embodiments, each of the forty vessel positions will be visited once before any of the forty reaction vessels is visited by a particular position (e.g., stirring position, sample dispensing position, or reagent dispensing position) for the second time.

In some embodiments, some or all of the stirring position, the sample dispensing position, and the reagent dispensing position constitute the same position. One of ordinary skill in the art would clearly understand that the reaction tray is not necessarily required to rotate three times and stops at three positions so long as the intended purposes of various embodiments are fulfilled. For example, the reaction tray may rotate and stop at more than three positions so long as each vessel position is visited once before any of the vessels is visited for the second time or so long as each vessel position stops at various positions required to complete the test. For example, in the above embodiments with forty vessel positions (and thus forty vessels), the reaction tray may rotate and pass nine vessel positions after the first rotation during an operating cycle, 10 vessel positions after the second rotation during the same operating cycle, 13 vessel positions after the third rotation during the same cycle, and nine vessel positions after the fourth and final rotation during the same operating cycle.

In this manner, each vessel stops at all the positions required for the test once before any vessel is visited for the second time at any of the positions required for the test. Therefore, the 9-23-9 operating cycle and the 9-10-13-9 operating cycle may be used for the same tests although the 9-10-13-9 operating cycle may be a little less efficient, assuming that the rotation speed remains substantially the same. In another example with forty vessels, the 9-23-9 operating cycle and the 9-63-9 operating cycle may be used for the same tests although the 9-63-9 operating cycle may be a little less efficient, assuming that the rotation speed remains substantially the same. One of ordinary skill in the art would clearly understand that rotating and passing a given number of vessel positions serves a substantially the same purpose as rotating and passing a total number of vessel positions which is equal to the sum of the given number of vessel positions plus a second number of complete rotation of the reaction tray. That is, a rotation and stop that passes 23 vessel positions serves substantially the same purposes as rotation and stop that passes 63, 103, 143, etc. positions for a reaction tray with forty vessels.

In some embodiments, the sample, it may be desirable to pipet and dispense the first reagent, and the second reagent in a certain order. For example, certain tests may desire or require that the first reagent be first dispensed into a reaction vessel followed by the test sample and then the second reagent in some embodiments. In these embodiments, the analyzer may dispense two or more of the test sample, the first reagent, and the second reagent may be dispensed into one or more reaction vessels while some reaction vessels remain empty.

In some embodiments, the analyzer is configured to cause the reaction tray to rotate during a first number of rotation periods and to stop during a second number of stop periods to optimize the sample test. In some embodiments, the first number is identical to the second number. In some embodiments, the first number is three. In some embodiments, the second number is three. In some embodiments, the first number of rotation periods or the second number of stop periods is configured to optimize an overall efficiency of the analyzer while allowing the single probe to perform the pipetting and dispensing actions for the intended purpose.

For example, in a reaction tray with 40 reaction vessels, the first number of rotation periods may be configured to allow the reaction tray to rotate during three rotation periods during an operating cycle wherein the reaction tray passes nine reaction vessel positions during the first rotation period, 23 vessel positions during the second rotation period, and seven vessel positions during the third rotation period. In this example, the analyzer is configured to cause the single probe to pipet and dispense the test sample, the first reagent, and the second reagent according to a sequence as required by the test. In this way, the analyzer is configured to optimize the test by minimizing the number of vessel positions passed during one operating cycle to be 39. In this example, the analyzer is configured to allow one single probe to complete the pipetting and dispensing operation for all vessels. In this test, the analyzer is configured to optimize the test by minimizing the number of vessel positions passed to be 39.

The optimization aspect may be explained as follows. As another example, since the analyzer needs to be configured in a way that each vessel position is visited to receive the test sample, the first reagent, and the second reagent, the analyzer may be configured to rotate during three rotation periods where the reaction tray rotates and passes nine vessel positions during the first rotation period, 23 vessel positions during the second rotation period, and 11 vessel positions during the third and final rotation period in an operating cycle. In this example, the reaction tray rotates and passes through 43 vessel positions during each operating cycle, and thus each position will be visited as in the previous example. Nonetheless, the reaction tray needs to rotate 43 vessel positions for each operating cycle which is clearly less efficient when compared to the previous example where the reaction tray needs to pass only 39 vessel positions for each operating cycle to achieve the same purpose. One of ordinary skills in the art will clearly understand that these numbers of vessel positions passed used in the above examples are for illustration and explanation purposes and do not intend to limit the scope of various embodiments as such, and that other combinations may also exist to achieve identical or similar purpose.

In some embodiments, the analyzer is configured to pass a number of vessel positions where the number equals to the total number of reaction vessels minus one. In these embodiments, it is advantageous in that contiguous reaction vessels will be visited sequentially so replacement of the reaction vessels is much easier, and multiple contiguous reaction vessels within which the measurement is already completed may be cleaned by multiple cleaning heads at the same time. Where the analyzer is configured such that non-contiguous reaction vessels are visited sequentially in some embodiments, the replacement of reaction vessels within which the measurement is already completed or the cleaning of these reaction vessels may be more complex. This illustrates another aspect of configuring the first number of rotation periods or the second number of stop periods to optimize the sample test.

The first time stop, 11a, is defined as the start of the operating cycle in some embodiments. During or at the first time stop, 11a, if the reaction vessel which stops at the sample dispensing position 101 of the reaction tray needs dispensing the sample thereinto during the current operating cycle, the probe 31 performs the following sequence of operation of sample dispensing in some embodiments. Firstly, the probe 31 ascends from the probe cleaning cell 90 and moves, 12a, to a position above the probe cleaning cell 90, then rotates, 12b, to a position above the sample/reagent suction position 203 of the sample/reagent tray 21, and subsequently descends, 12c, into the sample container 24.

After pipetting, 12d, a certain amount of sample according the set of the sample testing, the probe 31 ascends, 12e, and rotates, 12f, to a position above the sample dispensing position 101 of the reaction tray in some embodiments. After a certain moment M1, the probe 31 descends, 12g, into the reaction vessel and dispenses, 12h, a certain amount of sample. After the operation of sample dispensing is completed, the probe 31 ascends, 12i, and rotates, 12j, to a position above the probe cleaning cell 90 and then descends, 12k, into the probe cleaning cell 90, the cleaning, 121, of inner and outer walls of the probe 31 is performed in some embodiments. After the operation of cleaning, the probe 31 stops, 12m, in the probe cleaning cell 90 in some embodiments. If the reaction vessel stopping at the sample dispensing position 101 of the reaction tray does not require the sample dispensing during the current operating cycle, the probe 31 will keep still in the probe cleaning cell 90 and the above-mentioned operation sequence of sample dispensing will not be performed in some embodiments.

At some moment M2 after the probe 31 completes the operation of sample dispensing, 12h, and ascends, 12i, to above the reaction tray 11, the reaction tray 11 starts to perform the first time rotation, 11b in some embodiments. If the probe 31 does not perform the operation of sample dispensing during the current operating cycle, the reaction tray 11 still starts to perform the first time rotation, 11b, at the same moment M2 in some embodiments. During the first time rotation, the optical detector 50 performs the first time photoelectric measurement, 10b, during the current operating cycle in some embodiments. After photoelectric measurements of the reaction vessels passing through the photoelectric measurement position 104 are performed in turn, the reaction tray 11 may be stopped at a specified position in some embodiments.

During the first time rotation, the reaction tray 11 rotates for a total of nine vessel positions or a certain number of complete loop(s) plus nine vessel positions in the clockwise or counter-clockwise direction so as to accomplish photoelectric data collection and to ensure that the reaction vessel which needs a first reagent dispensing during the current operating cycle stops at the sample dispensing position 101 of the reaction tray in some embodiments. While the reaction tray starts to rotate and slows down to stop, the reaction tray is in a non-uniform motion status, which may adversely affect the reliability of the photoelectric data collection in some embodiments. Therefore, the photoelectric data collection may be performed which the reaction tray is in a status of substantially uniform motion. One of ordinary skill in the art would clearly understand that a mechanism may be in a status of substantially uniform motion due to manufacturing and/or operation tolerances and/or allowances even though the mechanism is designed or intended to be in a status of absolutely uniform motion. Manufacturing tolerances and allowances are well known. Operation tolerances and allowance may comprise, for example, fluctuations in the pneumatic or electrical power supply.

At or after the end of the first time rotation, 11b, the reaction tray comes to the second stop, 11c, in some embodiments. During this stop period, the probe 31 may dispense a first reagent into the reaction vessel which stops at the sample dispensing position 101 of the reaction tray as needed in some embodiments. In some embodiments, the sample dispensing position 101 may also be referred to as reagent dispensing position. The sample dispensing position may be the same as the reagent dispensing position, and they may both be the 1# position of the reaction tray in some embodiments.

If the reaction vessel which stops at the sample dispensing position 101 needs some first reagent dispensed therein during the current operating cycle, during the first time rotation, 11b, of the reaction tray, and after the probe 31 finishes the operation sequence of sample dispensing, it may be started at a certain moment M3 to perform a sequence of operation of first reagent dispensing, 13a, 13b, 13c, 13d, 13e, 13f, 13g, 13h, 13i, 13j, 13k, 131, and 13m in some embodiments. Thus, in some embodiments where the second time stop, 11c, of the reaction tray comes, the probe 31 may immediately or shortly after add a first reagent into the reaction vessel which stops at the sample dispensing position 101 of the reaction tray so as to save time in some embodiments.

The sequence of operation for the first reagent dispensing is similar to that for the sample dispensing with some difference in, for example, pipetting a certain amount of first reagent from a reagent container which stops at the sample/reagent pipetting position 203 of the sample/reagent tray 21 in some embodiments, and thus it will not be repeated herein. In some embodiments where the reaction vessel that stops at the sample dispensing position 101 of the reaction tray during the current operating cycle does not require the operation of first reagent dispensing, the probe may be kept still in the probe cleaning cell 90, and the operation sequence of first reagent dispensing will not be performed in some embodiments.

The second time stop, 11c, of the reaction tray lasts till a certain moment M4, and then the second time rotation, 11f, starts in some embodiments. During the second time rotation, the optical detector 50 performs the second time photoelectric measurement, 10c in some embodiments. After the optical detector 50 performs photoelectric measurements of the reaction vessels passing through the photoelectric measurement position 104 in turn, the reaction tray 11 stops at a specified position in some embodiments.

During this rotation period, the reaction tray continuously rotates for twenty-three vessel positions or for a certain number of loop(s) plus twenty-three vessel positions in the clockwise or counterclockwise direction so as to accomplish the photoelectric data collection and ensure that the reaction vessel which needs a second reagent to be dispensed therein during the current operating cycle may stop at the sample dispensing position 101 of the reaction tray in some embodiments. One of ordinary skill in the art would clearly understand that the optical detector 50 may also perform photoelectric measurement at least once during each operating cycle in some embodiments. Nonetheless, the optical detector 50 may perform the photoelectric measurements at least twice during each operating cycle in some embodiments. Because the time interval of sampling is shortened, the accuracy of test results may therefore be enhanced.

In some embodiments, that the second time stop, 11c, of the reaction tray lasts till a certain moment M4 later and then the second time rotation, 11f, is started may serve two purposes in some embodiments. The first purpose served is to ensure that the time interval between the two times of photoelectric data collection during each operating cycle is equal to one half of the operating cycle so as to ensure that a time interval of sampling of an item is uniform in some embodiments. In some embodiments the sampling time interval may be uniform. In some embodiments, a non-uniform sampling time interval may also be employed based on the need in the arrangement of the timing sequences during the operating cycle. The other purpose served is to ensure compatibility with the automatic cleaning function of reaction vessels which will be described in subsequent paragraphs in greater details.

After the second time rotation, 11f, of the reaction tray is completed, the third time stop, 11g, starts in some embodiments. During the third time stop period, the probe 31 may add a second reagent into a reaction vessel which stops at the sample dispensing position 101 of the reaction tray as needed or required in some embodiments. If the reaction vessel which stops at the sample dispensing position 101 during the current operating cycle needs the second reagent dispensed thereinto, during the second time rotation, 11f, of the reaction tray and after the probe 31 completes the operation sequence of first reagent dispensing, it starts after a certain moment M5 to perform an operation sequence of second reagent dispensing, 14a, 14b, 14c, 14d, 14e, 14f, 14g, 14h, 14i, 14j, 14k, 14l, and 14m in some embodiments.

Thus, when the reaction tray stops for the third time, 11g, the probe 31 may immediately or shortly after dispenses the second reagent into the reaction vessel which stops at the sample dispensing position 101 of the reaction tray in some embodiments. In some embodiments, the probe 31 may immediately or shortly after dispenses the second reagent into the reaction vessel which stops at the sample dispensing position 101 of the reaction tray so as to save time. The sequence of operation for dispensing the second reagent is similar to the sequence of operation for dispensing the sample and the first reagent with possible difference in, for example, retrieving a certain amount of the second reagent from a reagent container which stops at the sample/reagent suction position 203 of the sample/reagent tray 21, and thus it will be not repeated herein. In some embodiments where the reaction vessel which stops at the sample dispensing position 101 of the reaction tray during the current operating cycle does not require the operation for dispensing the second reagent, the probe 31 may be kept still in the probe cleaning cell 90, and the operation sequence of second reagent dispensing may be spared.

During the third time stop, 11g, of the reaction tray 11, after the probe 31 dispenses, 14h, the second reagent and ascends, 14i, to a position above the reaction tray, the reaction tray 11 starts the rotation for the third time, 11h, in some embodiments. The reaction tray 11 rotates nine vessel positions and then stops, 11i, in some embodiments. After the probe 31 completes the cleaning, 14l, the current operating cycle is completed. In some embodiments where there is no need to perform the sequence of operation for dispensing the second reagent during the current operating cycle, the reaction tray still operates in the same manner in some embodiments. In these embodiments, after the rotation for the second time, 11f, is completed, the reaction tray remains still during 11g, then rotates, 11h, nine vessel positions and stops, 11i, to remain still for a period of time, and then the current operating cycle is completed in some embodiments.

During each operating cycle, the sample may be dispensed into the reaction vessel which stops at the sample dispensing position 101 of the reaction tray during the first time stop, 11a, of the reaction tray in some embodiments. In these embodiments, after the reaction tray rotates nine vessel positions or a certain number of loop(s) plus nine vessel positions during the first time rotation, 11b, the reaction vessel that has been dispensed the sample therein during the current operating cycle just stops at the stirring position 103 of the reaction tray in some embodiments. At this time, the stirring rod 41 moves into the reaction vessel which stops at the stirring position 103 and performs the stirring operation in the reaction vessel in some embodiments.

In some embodiments, during each operating cycle, a second reagent may be dispensed into the reaction vessel which stops at the sample dispensing position 101 during the third time stop, 11g, of the reaction tray. In these embodiments, after the reaction tray rotates, 11h, nine vessel positions during the rotation for the third time, the reaction vessel into which the second reagent has been dispensed during the current operating cycle just stops at about the stirring position 103 of the reaction tray such that at the beginning of the next operating cycle the stirring rod 41 may move into the reaction vessel which stops at about the stirring position 103 and performs a stirring operation in the reaction vessel into which the second reagent has been dispensed in some embodiments.

In these embodiments, during the first time stop, 11a, and the second time stop, 11c, of the reaction tray, the stirring rod 41 performs the stirring operation after the dispensing of the second reagent and the stirring operation after the dispensing of the sample as needed or required by the sample testing processes in some embodiments. In these embodiments, while the reaction tray may periodically operate in certain manner, a stirring operation after the dispensing of the sample or the second reagent may be performed in time as required by the sample testing processes.

A sequence of operation for employing the stirring rod 41 is described below. The stirring rod ascends from the stirring rod cleaning cell 100, descends, 16a, into the reaction vessel, and performs the stirring operation 16b in some embodiments. In these embodiments, the stirring rod ascends from the reaction vessel, descends, 16c, into the stirring rod cleaning cell 100, and an action is performed for cleaning 16d the stirring rod in some embodiments. After the cleaning action, the stirring rod remains still 16e in the cleaning cell in some embodiments.

The sample/reagent tray 21 during each operating cycle performs rotation three times, 15b, 15c, 15d, as needed or required. The sample/reagent tray 21 may also rotate more or less than three times as required or needed. In some embodiments where the operation of dispensing the first reagent is needed during the current operating cycle, before the sequence of operation for the first reagent suction is performed during the current operating cycle, the sample/reagent tray 21 performs the rotation for the first time, 15b, and causes a reagent container to be filled with the required first reagent during the current operating cycle stop at the sample/reagent suction position 203 of the sample/reagent tray 21 in some embodiments. If the operation of dispensing the first reagent is not needed or required during the current operating cycle, or if the needed reagent container has been at about the sample/reagent suction position 203 of the sample/reagent tray 21, it may be unnecessary to perform the present rotation 15b in some embodiments.

In some embodiments where the operation of dispensing the second reagent is needed during the current operating cycle, before the sequence of operation for the second reagent suction is performed during the current operating cycle, the sample/reagent tray 21 performs the rotation for the second time, 15c, and causes the reagent container to be filled with the needed second reagent during the current operating cycle stop at the sample/reagent suction position 203 of the sample/reagent tray 21. If the operation of second reagent dispensing is not needed during the current operating cycle or the needed reagent container has been at about the sample/reagent suction position 203 of the sample/reagent tray 21, it may be unnecessary to perform the present rotation 15c in some embodiments.

In some embodiments where the operation of dispensing the sample is needed during the next operating cycle, before the end of the current operating cycle, the sample/reagent tray 21 performs the rotation for the third time, 15d, and causes a sample container to be filled with the sample needed in the next operating cycle stop at about the sample/reagent suction position 203 of the sample/reagent tray 21 in some embodiments. In some embodiments where the operation of dispensing the sample is not needed during the next operating cycle, or the needed sample container has been at about the sample/reagent suction position 203 of the sample/reagent tray 21, it may be unnecessary to perform the present rotation 15d in some embodiments. When the sample/reagent tray does not have to rotate, it keeps still 15a in some embodiments.

During an operating cycle, the optical detector 50 performs photoelectric data collections, 10b and 10 cm during the first time rotation, 11b, and the second time rotation, 11f, of the reaction tray respectively, and remains in a standby status 10a during other times in some embodiments.

The method for analyzing the samples in accordance with several embodiments may comprise an automatic reaction vessel cleaning action in some embodiments. Referring to FIG. 5 where the sample analyzer is configured with the automatic reaction vessel cleaning assembly 60, during an operating cycle of the sample analyzer 300, only one time rotation, 11d, and one time stop, 11e, need to be inserted during the second time stop period of the reaction tray and after the probe dispenses the first reagent and ascends from the reaction tray in some embodiments.

In these embodiments where the sequence of operation for dispensing the first reagent during the current operating cycle may not be needed, the added rotation, 11d, of the reaction tray may be started in advance in some embodiments. During the added rotation, the reaction tray rotates nineteen vessel positions and then stops, 11e, in some embodiments. During the stop period, the automatic reaction vessel cleaning head 61 descends, 17b, into the reaction vessel, performs an operation of cleaning, 17c, and then ascends, 17d, to a position above the reaction tray in some embodiments. At some other times, the automatic reaction vessel cleaning head remains still 17a in a position above the reaction tray in some embodiments. All the other operation sequences may not be affected.

Figure 6:
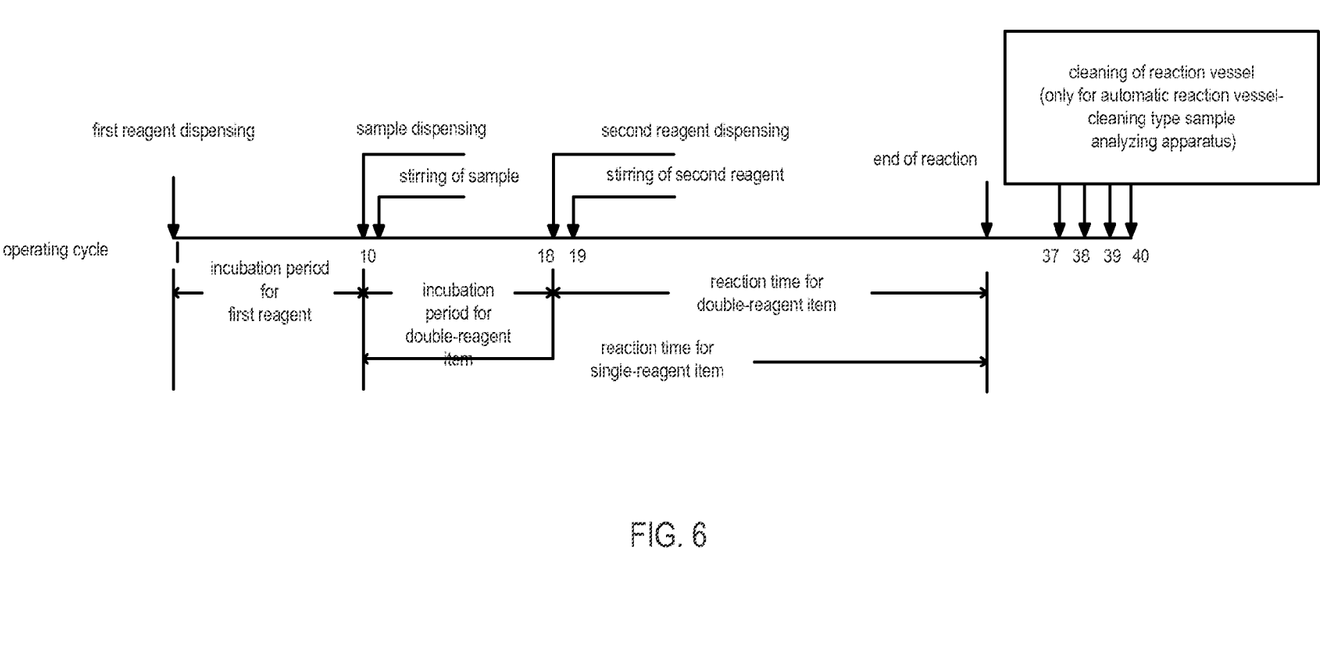
FIG. 6 illustrates a schematic test flow chart of a sample analyzer in accordance with some embodiments.

FIG. 6 illustrates a test flow chart of the sample analyzer 300 in accordance with some embodiments. A test is used here as an example to illustrate and explain the testing processes of the sample analyzing apparatus. The test described herein does not intend to and shall not be interpreted as limiting the scope of various embodiments of the invention. For a given test, an operating cycle during which a first reagent is dispensed is defined as the first operating cycle. During the first operating cycle, at about the second time stop, 11c, of the reaction tray, a first reagent may be dispensed into a clean reaction vessel which stops at around the sample dispensing position 101 of the reaction tray in some embodiments.

After an incubation period for a first reagent, for example, at the start of the tenth operating cycle, during the first time stop, 11a, of the reaction tray, the reaction vessel into which a first reagent has been dispensed during the first operating cycle, stops at around the sample dispensing position 101 of the reaction tray again, whereupon the probe 31 adds a sample into the reaction vessel in some embodiments. After the reaction tray performs the first time rotation, 11b, during the current operating cycle, the reaction vessel stops at the stirring position 103 of the reaction tray, performs the operation of stirring in some embodiments.

If the test is a single-reagent item, the reaction starts at this time. After eliminating or significantly reducing undesirable reactions using a fixed incubation period, i.e., incubation period for double-reagent item, for example, at the eighteenth operating cycle, during the third time stop, 11g, of the reaction tray, the reaction vessel into which a first reagent and a sample have been in the first and tenth operating cycles respectively, stops at about the sample dispensing position 101 of the reaction tray again in some embodiments. If the test is a double-reagent item, a second reagent may be dispensed at this time, and then the reaction tray performs the rotation for the third time, 11h, to cause the reaction vessel to stop at about the stirring position 103 of the reaction tray, where a stirring operation may be performed at the beginning of the next operating cycle and then the reaction starts in some embodiments.

In some embodiments where the test comprises the single-reagent item, the operation of dispensing the second reagent may not be needed during the current operating cycle. In these embodiments, the stirring operation may also not be needed at the beginning of the next operating cycle.

Regardless of the single-reagent item test or the double-reagent item test, after the beginning of the reaction, when a user prescribed reaction time period, e.g. reaction time for single-reagent item or reaction time for double-reagent item, elapses after a certain number of operating cycles, the test ends in some embodiments. During an operating cycle, the optical detector 50 performs photoelectric data collection twice to collect photoelectric data corresponding to respective wavelengths in relation to all the reaction vessels in some embodiments. In these embodiments, test results may be obtained by selecting appropriate optical measurement data to perform a related calculation according to various needs of different items. The time interval between two optical measurement points for each item may be equal to one half of the operating cycle in some embodiments.

In some embodiments where the sample analyzer is not configured with the automatic reaction vessel cleaning assembly 60, after a batch of tests on the reaction tray is completed, the used reaction vessels may be rotated to the reaction vessel replacement positions 106 subject to the control of a corresponding reaction vessel replacement instruction and then manual reaction vessel replacement operations may be performed in some embodiments.

In some embodiments where the sample analyzer is configured to be equipped with the automatic reaction vessel cleaning assembly 60, and where the operating cycle involving a first reagent dispensing operation for a test item is defined as the first operating cycle of the test, after the first time rotation, 11b, of the reaction tray in the thirty-seventh operating cycle, the reaction vessel stops at the 37# position in some embodiments. In these embodiments, the reaction tray then rotates, 11d, nineteen vessel positions in the clockwise or counterclockwise direction depending on the configuration, the reaction vessel stops at the first position of the cleaning positions 105 of the reaction tray, and the first stage cleaning may be performed in some embodiments. Such a sequence of operation may be repeatedly performed, and thus during the fortieth operating cycle, the reaction vessel rotates to the fourth position of the cleaning positions 105 of the reaction tray, and the fourth stage cleaning may be performed in some embodiments.

The cleaning for the reaction vessel is then completed in some embodiments. During the next operating cycle, the cleaned reaction vessel stops at about the sample dispensing position 101 of the reaction tray during the second time stop, 11c, of the reaction tray, where the operation of dispensing the first reagent may be performed to start a new test in some embodiments.

The sample analyzer may operate sequentially according to the aforementioned sequences of operation and may perform sequences of operation for dispensing the samples or for dispensing and/or stirring the reagents and so on for different reaction vessels during each operating cycle so that one or more single-reagent item and/or double-reagent item tests may be accomplished efficiently in some embodiments. In some embodiments, the efficiency of the test for single-reagent items and double-reagent items may be identical or substantially identically; i.e., the test speed does not vary substantially with test items, regardless of whether the test items constitute single-reagent items or double-reagent items in some embodiments.

In some embodiments, the test speed for a single-reagent test is substantially the same as that for a double-reagent test. In these embodiments, the substantially the same test speed may be achieved by making the same stops at the same position(s) for dispensing the second-reagent even in the single-reagent test in which second-reagent is not required for the test. In some embodiments, the method or the apparatus does not stop at the position(s) for dispensing the second reagent in a double-reagent test which does not require the second reagent for the double-reagent test. In some embodiments where the sample analyzer is configured to comprise the automatic reaction vessel cleaning assembly 60, a constant speed for testing both single/double-reagent items may be achieved.

In some embodiments where the sample analyzer is configured not to comprise the automatic reaction vessel cleaning assembly 60, after the reagent(s) and/or sample(s) is dispensed into all of the reaction vessels on the reaction tray, the reaction vessel replacement operation may not be performed to start a new test until the end of the last reaction on the reaction tray so that the test may not be repeatedly performed. In these embodiments, a constant speed test may not be achieved, but the cost may be reduced because of the exclusion of the automatic reaction vessel cleaning assembly. In some embodiments, because the test speed remains substantially the same for both the single-agent items and the double reagent items, the efficiency of the test may still be relatively high. In some embodiments, the test speeds refer to the speeds of motion of various components of the biochemical analyzer. In some embodiments, the test speeds refer to the speeds for conducting the tests or the period(s) of time to conduct these tests.

In some embodiments, the sample analyzer may perform the function of automatic sample dilution which may be implemented as follows. When automatic sample dilution for a particular test is scheduled, during a certain operating cycle which is defined as the N-th operating cycle for the ease of explanation, distilled water may be dispensed into the clean reaction vessel which is situated in the sample dispensing position 101 of the reaction tray as a first reagent during the operation of dispensing the first reagent in some embodiments. During the operation of dispensing the first reagent of the (N+1)-th operating cycle, a first reagent for the test may be dispensed into the next reaction vessel which is situated in the sample dispensing position 101 of the reaction tray in some embodiments.

During the (N+9)-th operating cycle, a sample which needs to be diluted may be dispensed, during the operation of sample dispensing, into the reaction vessel which contains distilled water and is situated in the sample dispensing position 101 of the reaction tray again in some embodiments. In these embodiments, a stirring operation may then be performed, and the sample dilution operation is then completed. During the (N+10)-th operating cycle, the reaction vessel having the first reagent for the test dispensed therein stops at the sample dispensing position 101 of the reaction tray again during the operation of sample dispensing in some embodiments. At the same time, the reaction vessel having the diluted sample filled therein stops at the diluted sample suction position 102 of the reaction tray in some embodiments.

The probe 31 then pipets a certain amount of diluted sample from the reaction vessel at the diluted sample suction position 102 of the reaction tray in some embodiments. The probe then adds the certain amount of diluted sample into the reaction vessel in the sample dispensing position 101 of the reaction tray, and then the stirring operation may be performed in some embodiments. In some embodiments where the test comprises a single-reagent item, the reaction starts. In some embodiments where the test comprises a double-reagent item, a corresponding second reagent may be dispensed during the (N+18)-th operating cycle, where the stirring operation for the second reagent may be performed, and the reaction starts.

In some embodiments where the sample analyzer is configured to comprise the filter-wheeled photometer, the following advantages may be achieved. By combining the structural configuration of the sample analyzer with the method for analyzing samples, while the test performance may be ensured, the structural configuration may be simplified, and the cost may be significantly reduced. The testing process is relatively simple and is thus easy to carry out. The testing process with respect to the same test item may be fixed in some embodiments and thus ensures the repeatability of the test result and probably better test performance.

The first reagent and the second reagent may be dispensed during the same operating cycle, and thus an additional operating cycle may not be needed for dispensing the second reagent so that the analyzer exhibit identical or substantially identical test speed for both the single- and double-reagent items, and the efficiency of the test may be higher as compared with the prior art sample analyzer. The sample analyzer and the method for analyzing samples may further benefit from the use of disposable reaction vessels and automatic cleaning reaction vessels in some embodiments. In some embodiments, the method for analyzing samples may also comprise the sample automatic dilution function.

In some of the aforementioned embodiments, the sample analyzer comprises forty reaction vessels, and many aspects of the embodiments and examples described above such as the rotations, various positions, temporal sequence, etc., are based on the forty reaction vessel configuration. Nonetheless, it shall be noted that the forty vessel configuration is described above for the ease of explanation and illustration and does not intend and shall not be construed or interpreted to limit the scope of various embodiments. In fact, one of ordinary skill in the art will clearly understand various other configurations with other numbers of reaction vessels based upon the description herein so as to be able to make and use various embodiments of the invention.

In addition, relative spatial relationships between the operating positions of the reaction tray such as the sample dispensing position, the stirring position, the cleaning position, the photoelectric measurement position, the manual reaction vessel replacement position, and so on may be adjusted or changed while serving similar or identical purposes. Moreover, during an operating cycle, the reaction tray may rotate R loops plus or minus one vessel position in the clockwise or counterclockwise direction in some embodiments where R is an integer. In these embodiments, the reaction tray during one operating cycle may rotate one vessel position in either direction.

In some embodiments, the reaction tray may rotate R loops plus or minus N vessel positions in the clockwise or counterclockwise direction in some embodiments where R is an integer, and N is an integer which may be selected in a way that all reaction vessels will be visited during the operation. For example, for a reaction tray with 40 reaction vessels, N may be selected from integers such as 3, 7, 9, etc. To further illustrate this selection of integer N, the following example uses the example where the reaction tray is configured to accommodate 10 reaction vessels, and the reaction tray is configured to have N=3 and thus rotates and passes a total of seven (that is, 10 minus N equals 7) vessel positions during an operating cycle.

It may be easily seen that if vessel position #1 is visited during an operating cycle, vessel position #8 will be visited after the next cycle after the reaction tray rotates 7 positions, then vessel position #5 in the next operating cycle. Then vessel positions #2, #9, #6, #3, #10, #7, #4 will be visited in subsequent operating cycles before the vessel position #1 is visited again in the next operating cycle. Similarly, for N=3, it can also be demonstrated that all 10 positions will be visited when the reaction tray rotates and passes 13 vessel positions during an operating cycle. It can be seen that by selecting three for the integer N all the vessel positions will be visited in a sequence.

One of ordinary skill in the art will clearly understand, depending upon the number of reaction vessels in the reaction tray, other numbers may also be selected for N to achieve an identical or similar purpose. The sample dispensing of the sample dispensing operation sequence, the first reagent dispensing of the first reagent dispensing operation sequence, and the second reagent dispensing of the second reagent dispensing operation sequence may also be accomplished in different stop periods of the reaction tray in some embodiments. The two times of photoelectric data measurements applied to the reaction solution during each operating cycle may also be respectively performed during different rotation periods of the reaction tray in some embodiments. It is also understood that because the sample dispensing operation may be optional during at least some operating cycles, although the time interval from the start of a previous sample dispensing operation to the start of the next sample dispensing operation is defined as an operating cycle, the sample dispensing operation in which the sample is not dispensed is still considered as the start of the operating cycle in some embodiments.

In some embodiments where the sample analyzer performs the photoelectric data collection, each filters on the wheel which allow the lights with different wavelengths path through may be stopped at the photoelectric measurement position in turn. In these embodiments, the photoelectric measurements of the reaction vessels that sequentially pass through the photoelectric measurement position may be accomplished during a uniform rotation process of the reaction tray in some embodiments. In these embodiments, the filter wheel remains still during the period of photoelectric measurement, and the reaction tray rotates uniformly or substantially uniformly.

In the alternative or in addition to the aforementioned approach, the filter wheel may be kept rotating uniformly or substantially uniformly and the reaction tray delivers the reaction vessels which need the photoelectric measurement to the photoelectric measurement position in turn in some embodiments. In these embodiments, during a stop period of the reaction vessel and the process in which the filter wheel rotates one revolution, the photoelectric data collections for various wavelengths in relation to the reaction vessel may be accomplished. In some embodiments where the latter approach is adopted, in each operating cycle, the rotations of the reaction tray for the photoelectric data collections may exhibit some differences. For example, during each rotation, it may be necessary to cause the reaction tray to rotate a certain number of vessel positions within certain period of time in some embodiments. Moreover, starting from a particular vessel position, a number of reaction vessels stop at the photoelectric measurement position in turn so as to cause data to be collected. Thereafter, the reaction tray rotates a certain number of vessel positions within a certain time and then stops at a final position as required by the testing process in some embodiments.

In some embodiments where the sample analyzer comprises the optical detector, in addition to the use of the filter-wheeled photometer, other types of photometers, such as grating, multi-channel static filter, or other structure based photometers may also be used, while the other basic structural configurations of the sample analyzer remain similar or identical. In these embodiments, the sample analyzer may achieve identical or similar test efficiency for testing both single- and double-reagent items.

The aforementioned embodiments are described for the ease of illustration and explanation but do not intend to and shall not be construed to limit the scope of various embodiments. Modification and substitution may also be made by one of ordinary skill in the art without departing from the spirit or scope of the invention, which should still be deemed to be within the scope as set forth by the claims. Other aspects and features of the invention will be evident from reading the following detailed description of the preferred embodiments, which are intended to illustrate, not limit, the invention. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

The invention claimed is:

1. A method for analyzing a test sample via operating cycles that are all of a same type, where each operating cycle includes a previous sample dispensing operation and a next sample dispensing operation on a reaction tray comprising a plurality of reaction vessels, each operating cycle comprising:

rotating the reaction tray during a first number of rotation periods and stopping during a second number of stop periods;

dispensing a first reagent, a test sample, and a second reagent by a single probe respectively into the plurality of reaction vessels which stop at a sample and reagent dispensing position during respective periods of the second number of stop periods;

wherein the first number of rotation periods is at least three and the second number of stop periods is at least three.

2. The method of claim 1, wherein each operating cycle further comprises: performing a photoelectric measurement of a reaction solution comprising the test sample and one or more reagents in at least one of the plurality of reaction vessels.

3. The method of claim 2, wherein the photoelectric measurement comprises a first photoelectric measurement and a second photoelectric measurement, and the first photoelectric measurement and the second photoelectric measurement are respectively performed on the reaction solutions during respective rotation periods in the operating cycle.

4. The method of claim 1, wherein each operating cycle further comprises: mixing a reaction solution in one of the plurality of reaction vessels during a first stop period after dispensing the sample and a next stop period after dispensing the second reagent.

5. The method of claim 1, wherein the reaction tray comprises a diluted sample suction position which is located at a position adjacent to or near the sample and reagent dispensing position;

when the test sample needs to be diluted, dispensing a distilled water into a clean reaction vessel which stops at the sample and reagent dispensing position of the reaction tray during a first time period for dispensing the first reagent in a first operating cycle; dispensing the first reagent into a next reaction vessel which stops at the sample and reagent dispensing position during a second time period for dispensing the first reagent in a next operating cycle after the first operating cycle;

during a third time period of dispensing the sample in a second operating cycle, where the reaction vessel having the distilled water dispensed thereinto stops at the sample and reagent dispensing position again, dispensing the test sample that needs to be diluted into the reaction vessel and performing a stirring operation;

retrieving a certain amount of the diluted test sample from the reaction vessel at the diluted sample suction position in the reaction tray during the period of dispensing the sample in a next operating cycle after the second operating cycle;

where the reaction vessel having the first reagent dispensed thereinto stops at the sample and reagent dispensing position again, and where the reaction vessel having the diluted test sample filled therein stops at a diluted sample suction position in the reaction tray; and configuring the time interval between the second operating cycle and the first operating cycle to be an incubation period for the first reagent.

6. The method of claim 1, wherein each operating cycle further comprises: inserting one time of rotation into a first stop time period of the plurality of reaction vessels, wherein a fixed number of vessel positions are passed, and the reaction vessels which have finished reactions stop at one or more automatic cleaning positions in the reaction tray during the inserted rotation; and performing an automatic cleaning operation on the reaction vessels during a second stop period after the inserted rotation.

7. The method of claim 1, further comprising: performing a manual reaction vessel replacement operation after one or more tests.

8. The method of claim 1, wherein each operating cycle further comprises: dispensing the first reagent, then incubating the dispensed first reagent for a certain time; dispensing the test sample; and performing a mixing operation, wherein where a test is a single-reagent test, starting a reaction after dispensing the test sample and the act of performing the mixing operation, and where the test is a double-reagent item test, after the dispensing of the sample and completely eliminating undesirable reactions using a fixed incubation period, dispensing the second reagent and performing a second mixing operation to start a reaction.

9. The method of claim 1, wherein a number of rotated vessel positions minus a number of rotated integral loop(s) of vessel positions during each of the first number of rotation periods is a fixed value.

10. The method of claim 1, wherein a number of rotated vessel positions during all the first number of rotation periods is equal to a number of R loop(s) of vessel positions plus or minus a fixed integer value, wherein R is an integer and is greater than or equal to one.

11. The method of claim 10, wherein the fixed integer value is one.

* * * * *